United States Patent [19]

Yoshida et al.

[11] 4,284,353
[45] Aug. 18, 1981

[54] FLAW DETECTING APPARATUS

[75] Inventors: Hajime Yoshida, Chofu; Takashi Aoki, Sakai; Kei Nishida, Tokyo, all of Japan

[73] Assignees: Hajime Industries Ltd., Tokyo; Nihon Pillow Block Mfg. Co., Osaka, both of Japan

[21] Appl. No.: 57,419

[22] Filed: Jul. 13, 1979

[30] Foreign Application Priority Data

Jul. 17, 1978 [JP] Japan ................... 53/88799

[51] Int. Cl.³ ............................................. G01N 21/32
[52] U.S. Cl. ................... 356/240; 250/223 B; 250/227; 209/524
[58] Field of Search ............................... 356/240, 445; 250/223 B, 227; 209/524, 526

[56] References Cited

U.S. PATENT DOCUMENTS

| 3,349,916 | 10/1967 | Calhoun et al. | 356/240 |
| 3,631,255 | 12/1971 | Gender et al. | 356/240 |
| 3,639,067 | 2/1972 | Stevens | 356/240 |
| 3,786,238 | 1/1974 | Heisner | 250/227 |
| 4,001,579 | 1/1977 | Lebet et al. | 250/227 |

FOREIGN PATENT DOCUMENTS 2718802  11/1978  Fed. Rep. of Germany ....... 250/223 B Primary Examiner—R. A. Rosenberger

[57] ABSTRACT

A light source, a light projecting body, a plurality of optical fiber bundles and a sensor is provided. The light projecting body is provided with a central bore along which the sensor is aligned and a plurality of passages for a respective fiber bundle extending therethrough in communication with the central bore. The central bore is equal to or larger than the mouth of the bottle to be examined and the apertures terminate in connection with the central bore at a point lying in a circle on the central bore corresponding substantially to the periphery of mouth of the bottle, the longitudinal direction of the passages are substantially coincident with a tangent to their associated terminal point.

5 Claims, 7 Drawing Figures

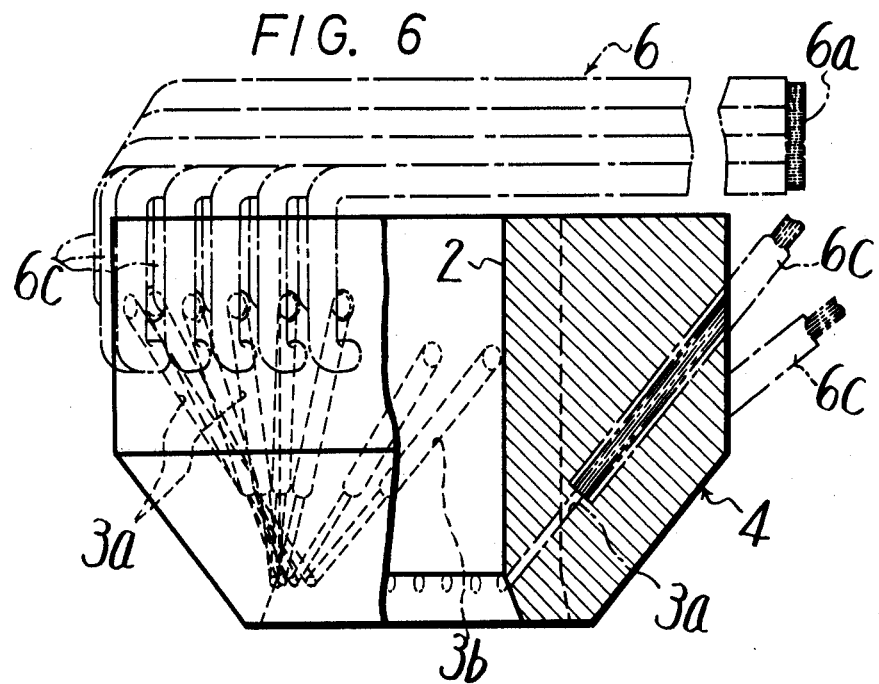
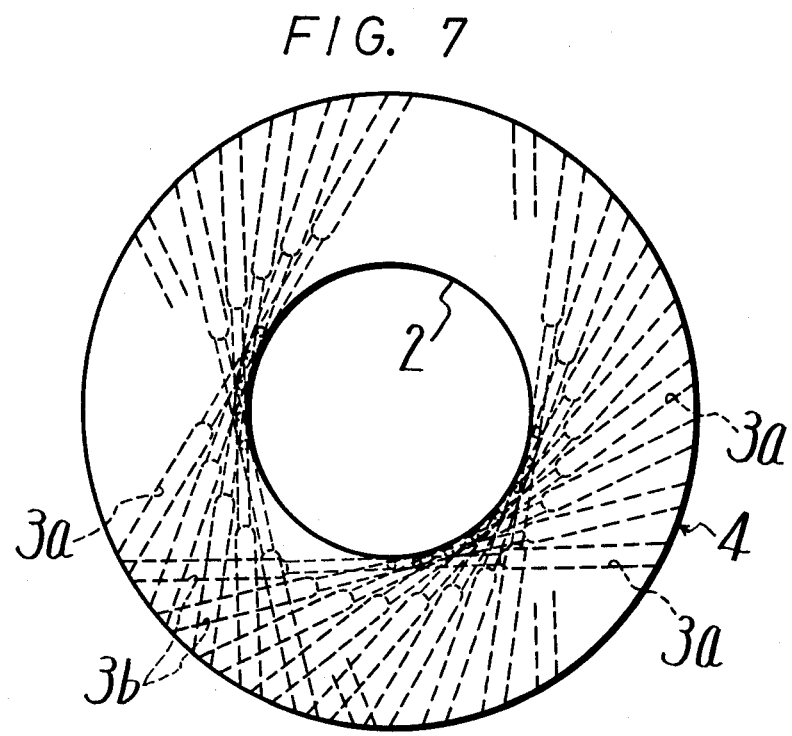

FLAW DETECTING APPARATUS

BACKGROUND OF THE INVENTION

1. Field of the Invention

The present invention relates to apparatus for detecting flaws such as checks, chippings, cracks or the like on the head of a bottle, and is directed more particularly to apparatus for detecting flaws such as cracks or the like on the lip or edge at the mouth or the head portion of a bottle for beverage, refreshments, beer and so on.

2. Description of the Prior Art

As well known, if a bottle with such a flaw as a check, chipping, crack or the like on its mouth is filled with refreshments, beverage, beer or the like and then to be sealed by a crown cap, leakage or other troubles may occur when or after the bottle is crowned or capped. Therefore, it is necessary to detect certain flaws immediately before the bottle is filled with its contents and capped.

In the prior art, the detection of flaws on the bottle mouth is carried out by the naked or unaided eye. This prior art detection by the naked eye requires rather long continued concentration for an observer and is not really effective due to human error and fatigue.

Other methods proposed in the art to detect flaws on a bottle mouth utilize light from a plurality of light sources which is irradiated on the bottle mouth and the reflected light on the bottle mouth is received by a television camera or photo-cell arrays. Such methods, however, are impractical because it is rather difficult to irradiate the bottle mouth or head of the bottle to be tested uniformly with light from a number of light sources and shades of bright and dark are likely appear on the bottle head which deteriorate the flaw detection results.

An object of the invention is to provide apparatus for detecting a flaw such as a check, chipping, crack or the like on the head or mouth of a bottle accurately and automatically.

Another object of the invention is to provide an apparatus for detecting a flaw such as check, chipping, crack or the like on a bottle mouth in which a number of optical fiber bundles are located between a single light source and the bottle mouth, whose flaws are to be detected, to transmit the light therethrough from the single light source to the bottle mouth, and the light reflected on the bottle mouth is received by a sensor such as a television camera.

According to an aspect of the present invention, there is provided a flaw detecting apparatus which comprises a light source, a number of optical fiber bundles each having one end facing the light source for transmitting light therefrom to the other ends. A light projecting body having a center bore and a number of apertures formed through the body is provided so that, the center bore has an inner diameter approximately equal to or larger than the outer diameter of a head of a bottle whose flaw or the like is detected. The apertures are so formed that they each lie on a tangential line to one of a number of points lying in a circle on the center bore, which substantially corresponds to the peripheral edge of the head of the bottle. The aperatures are inclined upwards and outwards with respect to the lower portion of the center bore, and their inner ends communicate with the center bore at the lower portion thereof. An optical fiber bundle is inserted into the aperture to a position near the center bore so as to irradiate the head of the bottle. A sensing device for picking up an image of the head of the bottle is provided in alignment with the center bore.

Other objects, features and advantages of the present invention will be apparent from the following description taken in conjunction with the accompanying drawings through which the like references designate the same elements and parts.

BRIEF DESCRIPTION OF THE DRAWINGS

FIG. 6 is a side view showing, partially in cross-section, a further example of the light projecting body useable in the invention; and FIG. 7 is a bottom view of the body shown in FIG. 6.

DESCRIPTION OF THE PREFERRED EMBODIMENTS

An example of the apparatus for detecting a flaw such as check, chipping, crack or the like on the head or mouth of a bottle according to the present invention will be hereinafter described with respect to the attached drawings.

Figure 1:
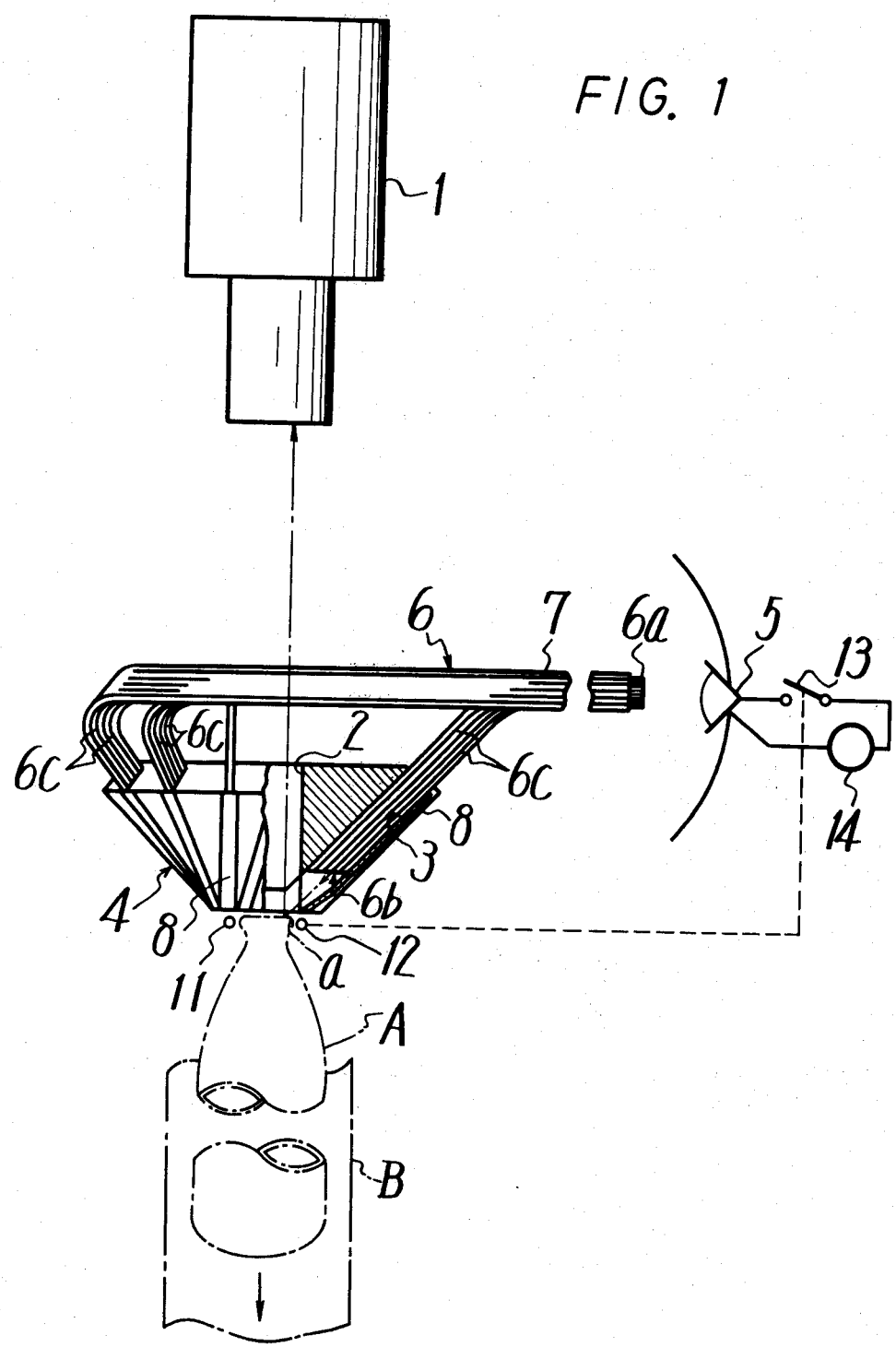
FIG. 1 is a schematic and systematic diagram showing an example of the flaw detecting apparatus according to the present invention.

In the example of the invention shown in FIGS. 1 to 3, there is provided a sensing device 1 such as a television camera which receives light reflected on the head or mouth of a bottle A to be detected through a center vertical bore 2 formed in a light projecting body of a circular post or frustoconical shape which will be described later. The light rom a single light source such as strobo-flash lamp 5 or the like irradiates the mouth or head of the bottle A, whose flaws such checks or the like should be detected, through an optical fiber bundle 6 which consists of a number of small optical fiber bundles 6c. Each of the small bundles consists of a plurality of optical fibers covered with a tubular cover 7 made of opaque material. The bundle 6 has one end 6a facing the single light source 5 and the other end portion divided into a number of small bundles, each of which passes through one of a plural member of slits 3 formed through a light projecting fixture or body 4 made of opaque material such as resin, plastics or the like. Each slit 3 is of uniform cross-section in the readial direction of the body 4. After a plurality of small bundles, each consisting of a number of optical fibers, are inserted into each of slits 3, the slits is provided with a cover 8 made of opaque material. The free ends 6b of the small bundles passing through the slits 3 are abraded in a horizontal or parallel direction to the peripheral edge a of the head or mouth of bottle A as shown in FIG. 1. Thus, the light from the light source 5 is projected onto the peripheral edge a or otherwise onto the lip surface of the bottle mouth as the case may require, of bottle A through the optical fiber bundle 6, and the light reflected from the peripheral edge a or lip surface of the mouth of bottle A is received by the television camera 1 through the bore 2 which is formed vertically through the center of the light projecting body 4 and which has the inner diameter substantially the same as the outer diameter of the peripheral edge a of the head of bottle A.

Figure 2:
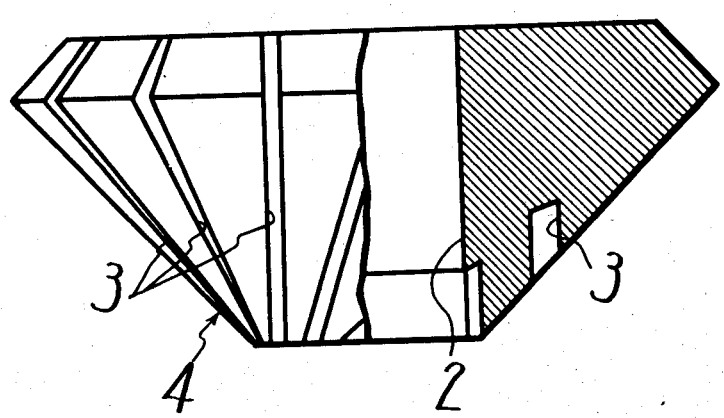
FIG. 2 is a side view showing, partially in cross-section, the light projecting body used in the example of the invention shown in FIG. 1.
Figure 3:
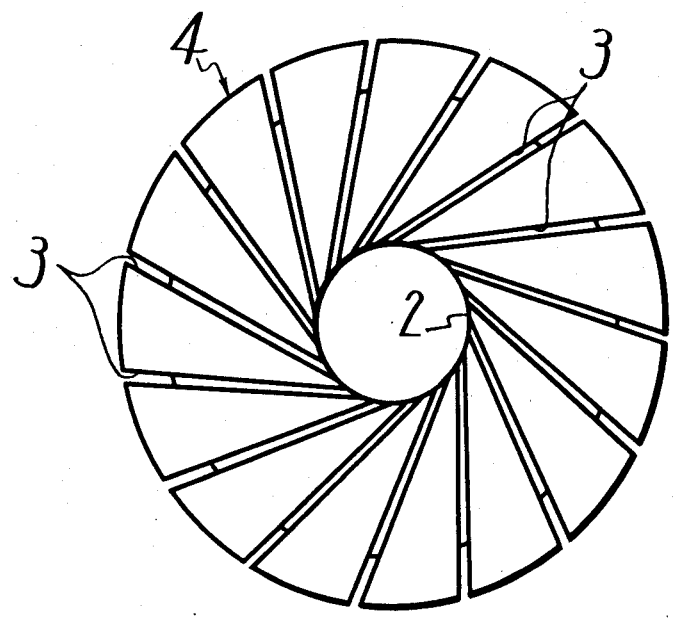
FIG. 3 is a bottom view of the body shown in FIG. 2.

In the example of the invention shown in FIGS. 1 to 3, the slits 3 are so formed in the light projecting body 4 that they extend outwards and obliquely upwards from the lower end portion of the center bore 2 which substantially corresponds to the outer diameter of the bottle mouth or peripheral edge a of bottle A, and they lie on the tangential lines to a number of points on the center bore 2 at a lower portion thereof or circular peripheral edge a of the head of bottle A when viewed from the upper or lower side of the body 4 as shown in, for example, FIG. 3. In this case, the number of points are equally located on the circle of the center bore 2 or peripheral edge a with a substantially same distance between adjacent ones. In this case, the lower end of each of the slits 3 communicates with the center bore 2 on the substantially same horizontal circular line near the lower end of center bore 2 and the upper end of each of the slits 3 is opened near the top portion of the light projecting body 4. A plurality of small optical fiber bundles 6c pass through each of the slits 3 from its upper opening to the portion near its lower opening and the ends thereof are abraded substantially horizontal as set forth above. Thus, the light emitted from the single light source 5 and passed through the optical fiber bundle 6 is irradiated on the peripheral edge a or lip surface of the bottle mouth as the case may require, uniformly from the end of each of the small oprical fiber bundles 6c in the slits 3.

When the peripheral edge a of the head of bottle A is irradiated by the light from the light source 5 through the bundle 6 located in the slits 3 formed in the light projecting body 4, if a flaw such as a crack or the like exists on the peripheral edge a of the head of bottle A, the irradiated light is scattered on the flaw. This scattered light is detected by the television camera 1. In other words, when the television camera 1 catches any scattered light, a flaw or the like exists on the peripheral edge a of the head of bottle A to be tested. If the television camera 1 detects no scattered light, it will mean that a bottle A has no flaw and hence the bottle A is useable.

In stead of a plurality of small bundles 6c, which are inserted into each of slits 3, a single bundle containing a number of optical fibers and having a cross-area substantially same as that of each of slits 3 can be of course used with the same effect.

In this invention, a detecting device is provided in connection with the light projecting body 4, which will detect that a bottle A, whose flaw or the like is to be detected and which is transported by, for example, a belt conveyer B, arrives at a predetermined detecting position, for example, beneath the vertical center bore 2 of the light projecting body 4, and at that time the light source such as a strobo-flash lamp 5 is lit by the detecting device. That is, as shown in FIG. 1, by way of example, a light source 11 such as a light emitting diode or the like and a photo-electric conversion element 12 such as a CdS or the like are provided on a fixed part (not shown) in connection with the light projecting body 4, especially its center bore 2 to form the above detecting device. In this case, the bottle A is transported such that between the top surface of bottle A and the bottom surface of light projecting body 4 there is provided a little gap for avoiding the top surface of bottle A from contacting with the bottom surface of body 4. When a bottle A is transported by the belt conveyer B to a predetermined detecting position as shown in FIG. 1, the light from the light source 11 to the photo-conversion element 12 is cut off by the bottle A. At this time, the photo-electric conversion element 12 operates to close a switch 13 inserted between the light source 5 such as a strobo-flash lamp and a power source 14, so that at this time the strobo-flash lamp 5 is flashed to irradiate the peripheral edge a of the head of bottle A through the optical fiber bundle 6. Thus, a flaw or the like existing on the head of bottle A can be detected by the television camera 1 as set forth above.

It is of course possible that an ordinary lamp such as a halogen lamp or the like be used in place of the strobo-flash lamp 5 to continuously supply the light therefrom through the optical fiber bundle 6. In this case, the switch 13 is always closed or is omitted.

As described above, according to the present invention, a single light source is employed, the light therefrom is transmitted through the optical fiber bundle consisting of a number of small optical fiber bundles and small optical bundles are inserted into a number of slits formed through the light projecting body with the attitude set forth above, so that the head of the bottle can be irradiated uniformly at high illumination intensity and hence the detection for flaws or the like on the head of the bottle can be performed with high accuracy.

In the above example of the invention, a plurality of small optical fiber bundles 6c are located in each of the slits 3, but it is possible that a single small optical fiber bundle 6c is used in each of the slits 3.

Figure 4:
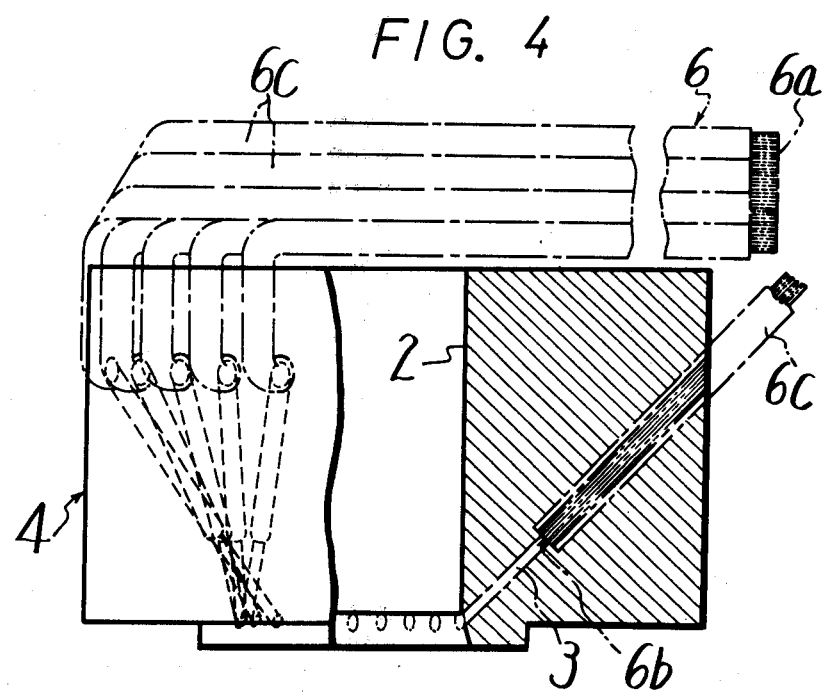
FIG. 4 is a side view showing, partially in cross-section, another example of a light projecting body which is also used in the invention.
Figure 5:
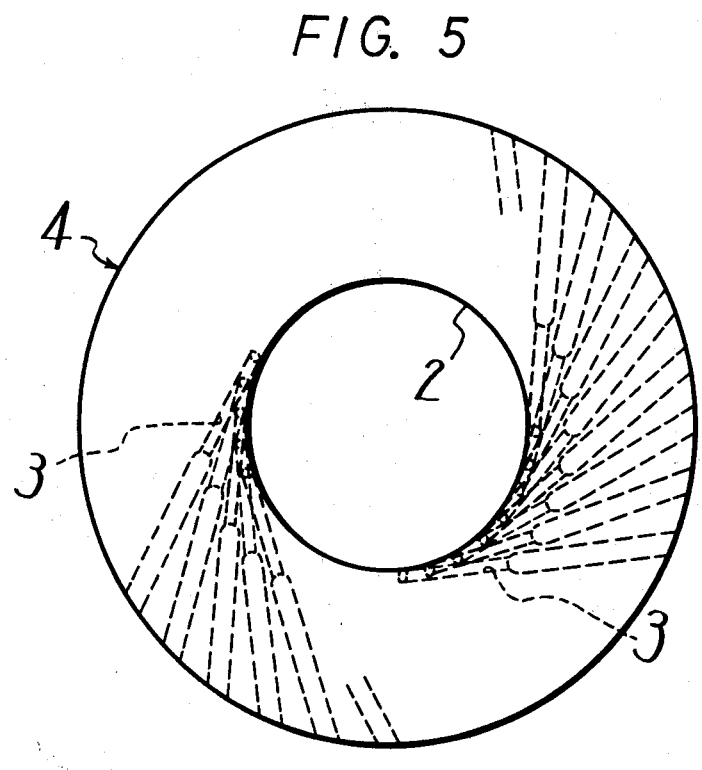
FIG. 5 is a bottom view of the body shown in FIG. 4.

FIGS. 4 and 5 show such an example. That is, as shown in FIG. 4 which is a side view showing, partially in cross-section, another example of the light projecting body 4 and in FIG. 5 which is a bottom view of FIG. 4, apertures 3 are formed through the light projecting body 4 in place of the slits 3 in the former example and a single small optical fiber bundle 6c is inserted into each of the apertures 3, or the cross-sectional area of each of the apertures 3 is selected approximately same as that of each of the small optical fiber bundles 6c. In this case, the attitude of the apertures 3 relative to the center bore 2 or the pheripheral edge a of the head of bottle A (not shown in FIGS. 4 and 5) is selected substantially same as that of the slits 3. The other construction of the light projecting body 4 of FIGS. 4 and 5 is substantially same as that shown in FIGS. 1 to 3.

FIGS. 6 and 7 are a side view partially in cross-section and a bottom view thereof for showing a further example of the light projecting device 4 which is also useable in the present invention. In this example, in order to irradiate the peripheral edge a of the head of bottle A (not shown in FIGS. 6 and 7) from different directions or angles, two set of apertures 3a and 3b, which are different in direction or inclination angle to each other with respect to the center bore 2 but lie on the tangential lines at the points on the central bore 2, when viewed from the upper or lower side of body 4 as shown in FIG. 7 similar to the foregoing examples, are formed through the light projecting body 4. In this case, a single small optical fiber bundle 6c is inserted into each of the apertures 3a and 3b similar to the example shown in FIGS. 4 and 5.

In this invention, it is not necessary that the contour of the light projecting body be limited to the illustrated examples but it can be selected desirably. And, the light projecting body can be made of such a material which is not transparent or is opaque such as plastics.

It will be apparent that many modifications and variations could be effected by one skilled in the art without departing from the spirits or scope of the novel concepts of the present invention, so that the scope or spirits of the invention should be determined by the appended claims only.

We claim as our invention:

1. Apparatus for detecting flaws in a bottle or the like, comprising:
   (a) a light source,
   (b) a light projecting body adapted to be located in opposition to the mouth of the bottle, the flaws of which are to be detected, said body having
      (i) a center bore the diameter of which is at least substantially equal to the outer diameter of the mouth of the bottle and,
      (ii) a plurality of elongated passages extending through said body in communication with said center bore, the longitudinal directions of each of said passages being substantially coincident with a line tangent to a respective one of a number of uniformly spaced points lying on said center bore in a circle corresponding substantially to the peripheral edge of the mouth of said bottle,
   (c) a plurality of optical fiber bundles, each of said bundles having one end facing said light source for transmitting light simultaneously through said bundles, and an other end extending through a respective one of said passages to illuminate the corresponding portion of the peripheral edge of the mouth of said bottle with light incident thereon in a direction predetermined by the direction of said passage,
   the number of said passages and associated fiber bundles being such that the entire peripheral edge of the mouth of said bottle is simultaneously illuminated and,
   (d) means arranged along the axis of said central bore for sensing the image of the illuminated mouth of the bottle through said center bore.

2. The apparatus, according to claim 1, wherein said passages extend through said body at an angle to the axis of said center bore inclined upwards and outwards from said center bore.

3. The apparatus, according to claim 2, wherein some of said passages extend at a first predetermined angle of inclination and other passages extend at second predetermined angle of inclination different from that of said first angle of inclination.

4. The apparatus, according to claim 1, 2 or 3, wherein said passages are slots formed in the surface of said body.

5. The apparatus, according to claim 1, 2 or 3, including a conveyor for transporting said bottle to a position opposed to said body and aligned with said center bore, said light source comprises a strobe-flash lamp, and including means for detecting the position of said bottle in alignment with said bore and for activating said strobe-flash lamp.

* * * * *